(12) United States Patent
Ubelhart

(10) Patent No.: US 12,178,397 B2
(45) Date of Patent: Dec. 31, 2024

(54) STERILE CALIBRATING CAP AND METHODS FOR USING THE SAME ON AN ENDOSCOPE

(71) Applicant: KARL STORZ Imaging, Inc., Goleta, CA (US)

(72) Inventor: Ray Ubelhart, Ventura, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 0 days.

(21) Appl. No.: 17/834,729

(22) Filed: Jun. 7, 2022

(65) Prior Publication Data

US 2023/0389777 A1 Dec. 7, 2023

(51) Int. Cl.
| | |
|---|---|
| *A61B 1/00* | (2006.01) |
| *A61B 1/05* | (2006.01) |
| *A61B 1/06* | (2006.01) |
| *H04N 17/00* | (2006.01) |
| *H04N 23/56* | (2023.01) |

(Continued)

(52) U.S. Cl.
CPC ...... *A61B 1/00137* (2013.01); *A61B 1/00057* (2013.01); *A61B 1/00144* (2013.01); *A61B 1/05* (2013.01); *A61B 1/0676* (2013.01); *A61B 1/0684* (2013.01); *H04N 17/002* (2013.01);
(Continued)

(58) Field of Classification Search
CPC ............ A61B 1/00137; A61B 1/00057; A61B 1/00144; A61B 1/05; A61B 1/0676; A61B 1/0684; H04N 17/002; H04N 23/56; H04N 25/63; H04N 23/555
See application file for complete search history.

(56) References Cited

U.S. PATENT DOCUMENTS 4,779,611 A * 10/1988 Grooters ............ A61B 1/00082
600/116
4,831,437 A   5/1989 Nishioka et al.
(Continued)

FOREIGN PATENT DOCUMENTS

CN   109655446 A  *  4/2019  .......... G01N 21/658
CN   211652028 U  * 10/2020
(Continued)

OTHER PUBLICATIONS

A High-Efficient Measurement System With Optimization Feature for Prototype CMOS Image Sensors, Klosowski, 2018, p. 2367 (Year: 2018).*

(Continued)

*Primary Examiner* — John P Leubecker
(74) *Attorney, Agent, or Firm* — David N. Villalpando; Jacqueline Cohen

(57) ABSTRACT

An endoscope includes a distal tip with a sterile cap disposed on the distal tip. The sterile cap reduces the exposure of the distal tip to contamination and includes an integrating sphere that enables calibration of an image sensor disposed in the endoscope. By enabling calibration of the image sensor while the sterile cap remains on the distal tip of the endoscope, the image sensor can be calibrated while maintaining the sterility of the endoscope. The sterile cap can be disposed on the distal tip of the endoscope under sterile conditions, placed in a sterile packaging, and can be removed just before a medical procedure to reduce the risk of exposing the endoscope to contamination.

19 Claims, 6 Drawing Sheets

(51) Int. Cl.
*H04N 25/63* (2023.01)
*H04N 23/50* (2023.01)

(52) U.S. Cl.
CPC ............ *H04N 23/56* (2023.01); *H04N 25/63* (2023.01); *H04N 23/555* (2023.01)

(56) References Cited

U.S. PATENT DOCUMENTS

| | | |
|---|---|---|
| 5,251,004 A | 10/1993 | Dorion et al. |
| 5,880,779 A | 3/1999 | Rhynes |
| 7,764,304 B2 | 7/2010 | Meron et al. |
| 8,040,496 B2 | 10/2011 | Leiner et al. |
| 9,060,676 B2 | 6/2015 | Blackhurst et al. |
| 9,492,060 B2 | 11/2016 | Blanquart |
| 9,913,574 B2 * | 3/2018 | Surti .................... A61B 1/0008 |
| 10,477,127 B2 | 11/2019 | Blanquart |
| 2002/0077677 A1 * | 6/2002 | Beck ................. A61B 1/00057 607/88 |
| 2003/0107726 A1 | 6/2003 | Hirt et al. |
| 2006/0069312 A1 * | 3/2006 | O'Connor ............ A61B 1/0008 600/176 |
| 2008/0204884 A1 * | 8/2008 | Jang .......................... G01J 1/02 359/599 |
| 2008/0228031 A1 | 9/2008 | Leiner et al. |
| 2009/0215160 A1 * | 8/2009 | Hatori ................ A61B 1/00057 435/287.4 |
| 2012/0289858 A1 | 11/2012 | Ouyang et al. |
| 2013/0331855 A1 * | 12/2013 | Smith ............. A61B 17/00234 606/114 |
| 2014/0362380 A1 * | 12/2014 | Harada ..................... G01J 1/08 356/402 |
| 2015/0091447 A1 | 4/2015 | Kubo |
| 2016/0174818 A1 | 6/2016 | Viering et al. |
| 2017/0243373 A1 * | 8/2017 | Bevensee ............... G03B 35/10 |
| 2019/0231175 A1 * | 8/2019 | Dreyer .................. A61B 1/015 |
| 2020/0211227 A1 * | 7/2020 | Nichol .................. H04N 23/55 |
| 2023/0115558 A1 * | 4/2023 | Ashizuka ............... A61B 1/018 600/104 |

FOREIGN PATENT DOCUMENTS

| | | | |
|---|---|---|---|
| JP | 2010-69244 A | | 9/2008 |
| JP | 2010069244 A | * | 4/2010 |
| JP | 2019148801 A | * | 9/2019 |
| WO | WO-2015064436 A1 | * | 5/2015 ......... A61B 1/00006 |

OTHER PUBLICATIONS

Fu, Y., X. Liu, et al., Miniaturized integrating sphere light sources based on LEDs for radiance responsivity calibration of optical imaging microscopes, Optics Express, Oct. 2020, V. 28, No. 21, Optica Publishing Group, Washington, D.C.

Martin, G., K. Muray, I. Reti, J. Dios, J. Schanda, Miniature integrating sphere - silicon detector combination for LED total power measurement, Measurement, Apr.-Jun. 1990, pp. 84-89, V. 8, No. 2, Elsevier, Amsterdam.

Klosowski, M., J. W. Jendernalik, et al., IEEE Transactions on Instrumentation and Measurement, Oct. 2018, pp. 2363-2372, v. 67, No. 10, IEEE, USA.

Mäki-Mantila, M., Extended European Search Report, Oct. 17, 2023, pp. 1-9, European Patent Office, Munich.

\* cited by examiner

STERILE CALIBRATING CAP AND METHODS FOR USING THE SAME ON AN ENDOSCOPE

BACKGROUND

The present disclosure is generally directed to devices, systems, and methods for calibrating an endoscope.

Endoscopic sensors may be calibrated to capture more accurate and less noisy readings. However, some sensors are not pre-calibrated, and are thus susceptible to various noise when generating readings. Endoscopes, and in particular sterile single use (SSU) endoscopes, are usually maintained in sterile packaging until just prior to use. As a result, attempting to calibrate the endoscope sensors to reduce susceptibility to noise could expose the scope to contamination and place a patient at risk.

SUMMARY

At least one exemplary embodiment is directed to a device including an endoscope having a proximal end and a distal tip, the endoscope including an image sensor disposed at least partially in the distal tip, and a cap configured to be disposed on the distal tip of the endoscope, the cap including an integrating sphere.

At least one exemplary embodiment is directed to a system including an endoscope having a proximal end and a distal tip, the endoscope including an image sensor disposed at least partially in the distal tip; and a cap configured to be disposed on the distal tip of the endoscope, the cap including an integrating sphere.

At least one exemplary embodiment is directed to a system including an endoscope having a proximal end and a distal tip, an image sensor disposed in the distal tip; an integrating sphere cap configured to be disposed on the distal tip and further configured to be removed from the distal tip, a processor; and a memory storing data thereon that, when processed by the processor, cause the processor to: produce light from an illumination source disposed within the endoscope, and receive a first light reading from the image sensor.

At least one exemplary embodiment is directed to a method that includes emitting light from an illumination source disposed in an endoscope, receiving a first reading from an image sensor disposed in the endoscope, the first reading based on the light emitted from the illumination source and passed through an integrating sphere, and calibrating, based on the first reading, a response of the image sensor.

At least one exemplary embodiment is directed to a method for calibrating and preparing to operate a sterile single use (SSU) endoscope, where the method includes disposing the endoscope in a sterile packaging, the endoscope including a removable cap covering a distal tip of the endoscope and the removable cap including an integrating sphere, and sealing the sterile packaging, where the endoscope is configured to connect to a processing unit, and perform a Dark Signal Non-Uniformity (DSNU) measurement.

At least one exemplary embodiment is directed to a device including an endoscope having a proximal end and a distal tip, the endoscope including an image sensor disposed at least partially in the distal tip; and a sterile spherical cap configured to be disposed on the distal tip of the endoscope and further configured to facilitate calibration of the image sensor.

At least one exemplary embodiment is directed to a sterile spherical cap configured to be disposed on a distal tip of an endoscope and further configured to facilitate calibration of an image sensor, the sterile spherical cap including: an integrating sphere, and an attachment mechanism configured to attach the sterile spherical cap to the distal tip of the endoscope.

DETAILED DESCRIPTION

Embodiments of the present disclosure will be described in connection with an endoscope. However, to avoid unnecessarily obscuring the present disclosure, the description omits a number of known structures and devices. These omissions are not to be construed as limitations of the scope of the claimed disclosure. Specific details are set forth to provide an understanding of the present disclosure. It should, however, be appreciated that the present disclosure may be practiced in a variety of ways beyond the specific detail set forth herein.

Figure 1A:
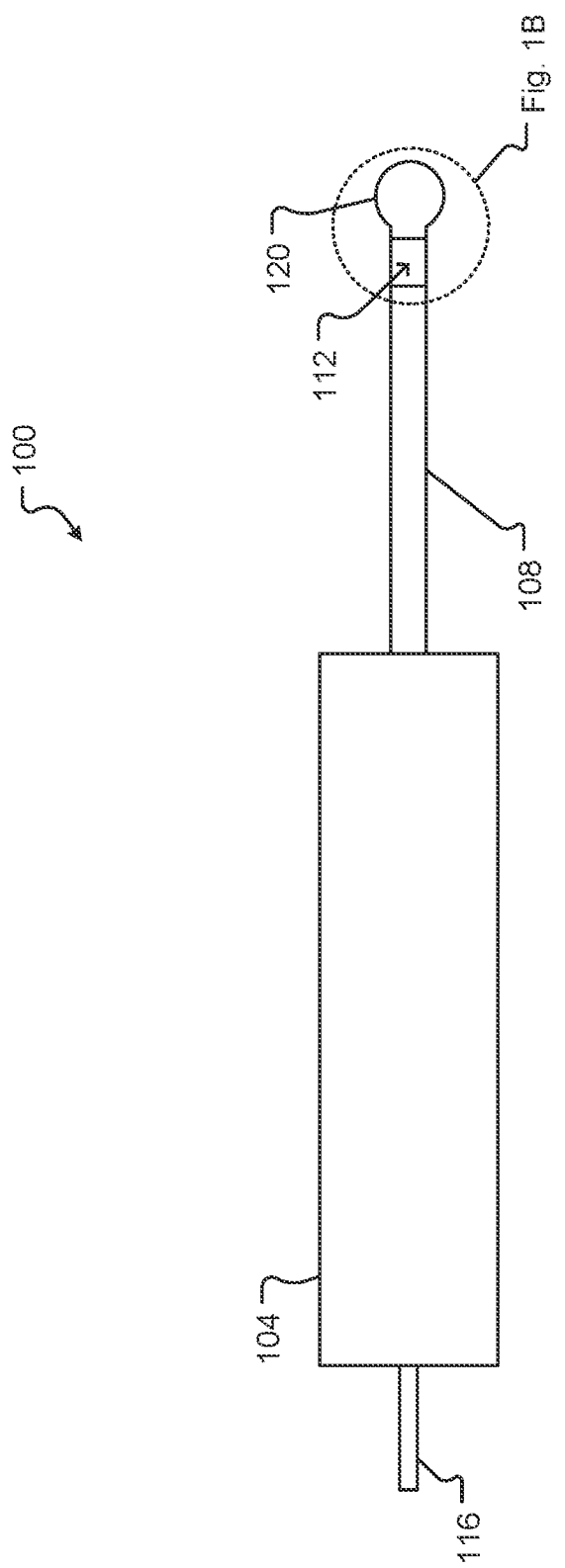
FIG. 1A illustrates an endoscope according to at least one exemplary embodiment.

FIG. 1A illustrates an endoscope 100 according to at least one exemplary embodiment. The endoscope 100 includes an endoscope body or handle 104, an elongated shaft 108, a distal tip region 112, a cable 116, and cap 120 comprising an integrating sphere. In some embodiments, for which the invention is particularly advantageous, the endoscope 100 is a SSU endoscope, however the disclosed technology is applicable to other endoscopic or optical observation instruments as well, including borescopes.

The endoscope body 104 provides a location for a user (e.g., a physician) to hold, manipulate, or control the endoscope 100. In some embodiments, an interior of the endoscope body 104 may include one or more hollow portions (not shown) capable of storing hardware components (e.g., cables/wiring, batteries, processing units, processors, cameras, image sensors, etc.) that enable one or more functions of the endoscope (e.g., illumination from the distal tip 112, image processing, etc.).

In some implementations, such as when the endoscope 100 is a SSU endoscope, the number of hardware components disposed in the endoscope 100 may be minimized and some may be absent. In other words, the hardware components and functions associated therewith, such as memory, image processing circuitry, certain illumination systems, and the like, may be respectively disposed and performed outside of the endoscope 100, for example in a camera control unit (CCU). In such implementations, expenses and waste may be beneficially reduced since the hardware components can be continuously re-used with multiple SSU endoscopes.

The distal end of the endoscope body 104 is connected to the elongated shaft 108, while the proximal end of the endoscope body 104 connects to the cable 116. In some embodiments, the endoscope body 104 may include one or more grips or grooves that assist the user with holding or manipulating the endoscope 100, as well as one or more controls (e.g., one or more buttons, levers, track pads, and/or switches) for controlling one or more functions of the endoscope 100.

The cable 116 may include one or more types of cables, such as optical, electrical, and/or fluid carrying cables, and may include insulated electrical wiring that passes power to the endoscope 100. In some embodiments, the endoscope 100 may include one or more buttons, levers, switches, or the like that enable the user to modulate, for example, the amount of power (e.g., current) flowing into the endoscope 100 for illumination, to cause the endoscope 100 to capture one or more images of a surgical site, to perform one or more calibration steps, to perform one or more image processing functions, to perform one or more physical actions, such as irrigation the surgical site or performing an angular deflection the distal tip of the endoscope, combinations thereof, and the like. For example, the user may activate a switch on the endoscope body 104 causing current to flow into the endoscope 100 through the cable 116 causing an illumination source within the endoscope 100 to emit light. In another example, the user may press a button on the endoscope body 104 that causes an imaging sensor 156 (shown in FIG. 1C) to capture illumination data for the purposes of calibrating the image sensor 156 of the endoscope 100. The cable 116 can also enable communication between the endoscope 100 and one or more external devices such as a power source, a display device, a processing unit (sometimes referred to as a camera control unit (CCU), combinations thereof, and/or the like. For example, the cable 116 may carry image data or measurements generated by the endoscope 100 in the form of electrical signals to a processing unit. The processing unit can then process the image data and render a resulting image or live video feed to a display unit.

The elongated shaft 108 is usually a thin tube that extends from the endoscope body 104 to the distal tip region 112. The elongated shaft 108 acts as an extension of the endoscope 100 such that the distal tip 112 can be introduced into a difficult to access region, such as the interior of a human or animal body. In some embodiments the shaft 108 is flexible, and it may be threaded or snaked through one or more portions of a patient to reach a target surgical or observation site. The shaft 108 therefore permits the distal tip 112 to connect to the endoscope body 104 during a medical procedure. For example, the endoscope 100 may be used to perform an observation of the esophagus of the patient, and the elongated shaft 108 may be passed down the throat of the patient until the distal tip 112 reaches the region of interest of the esophagus. The elongated shaft 108 enables the distal tip 112 to pass into the esophagus and provide data via the imaging sensor 156 (e.g., generate a live feed to a display unit, capture one or more images, etc.) without needing to position other portions of the endoscope 100 (e.g., the endoscope body 104) within the patient. In some embodiments, the elongated shaft 108 may comprise or be coated or covered in one or more rubber (e.g., polyurethane elastomer, polyester elastomer, etc.), plastic, insulating, and/or flexible materials, or may itself include one or more inert materials that prevent patient anatomy from reacting therewith.

The distal tip region 112 includes an illumination source by which light can be emitted as well as one or more sensors (e.g., image sensor, temperature probe, moisture sensor). The distal tip region 112 can be passed into the interior of a patient's body (e.g., through a natural orifice, such as down the throat of a patient when the esophagus is being examined by a physician, through a small incision, etc.) to a target anatomical site. The illumination source may be one or more light emitting diodes (LEDs), a laser, a light bulb, a lamp, the termination of a light guide, such as an optical fiber or fiber bundle, combinations thereof, and the like, capable of emitting light. The illumination source may illuminate an anatomical site (e.g., the upper esophagus), with such illumination enabling one or more image sensors to collect image data of the anatomical site. In one possible application, the illumination source may emit light on the upper esophagus, and the one or more image sensors may collect image data associated with the illuminated region. Such data can be passed to a processing unit, which may process the data and render an image depicting the data to a display or memory unit. Such imaging is of particular use to a physician in viewing the anatomical site in order to diagnose a disease, provide treatment, perform an operation, etc.

Figure 1B:
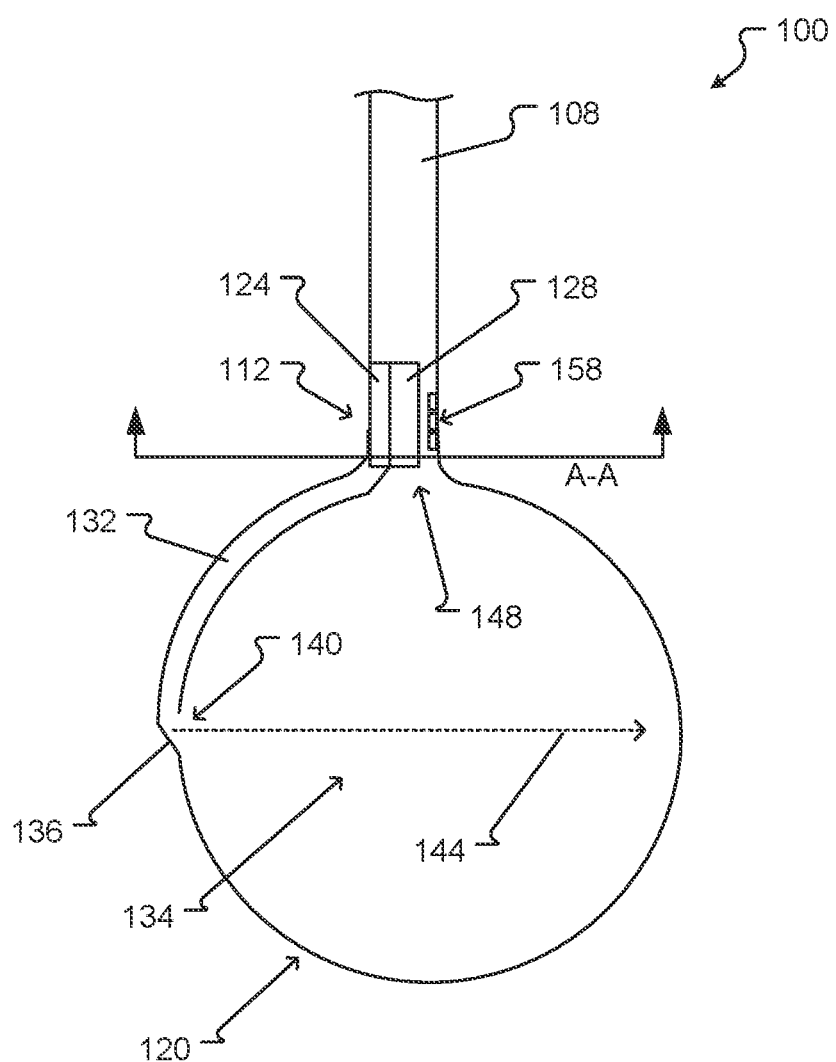
FIG. 1B illustrates a cap of the endoscope according to at least one exemplary embodiment.

Turning to FIG. 1B, the integrating sphere cap 120 is shown in accordance with at least one exemplary embodiment. The integrating sphere cap 120 is configured to be attached to and removed from the distal tip 112 of the endoscope 100. In some embodiments, the integrating sphere cap 120 may be disposed on the distal tip 112 of the endoscope 100 during production of the endoscope 100. In other words, the distal tip 112 may be sterilized and the integrating sphere cap 120 may be disposed on the endoscope 100 such that the distal tip 112 remains sterile until the endoscope 100 is used. In particularly preferred implementations, the entire endoscope 100 is sterilized, including the distal tip region 112 and the integrating sphere cap 120, and the two elements are assembled in a sterile environment, the entire system is then sealed in a sterile container, such as a plastic bag, until use. In other embodiments, the integrating sphere cap 120 may be separate from the endoscope 100 and may be configured to be disposed on the distal tip 112 of the endoscope 100 after the endoscope 100 has been connected to one or more processing units (e.g., one or more components of the system 200 discussed below) in order to enable calibration of the endoscope 100 preoperatively (e.g., before surgery) and/or intraoperatively (e.g., during surgery). In some embodiments, the integrating sphere cap 120 may be configured to be attached to the distal tip 112 of the endoscope 100 prior to sterilization. In such embodiments, the endoscope 100 may include one or more gas permeability ports 158 disposed near the output port 148 and/or within the integrating sphere cap 120. The gas permeability ports 158 may be sealed with one or more membranes to permit gas to permeate into the elongated shaft 108 to enable, for example, sterilization of the interior of the endoscope 100. In other words, the gas permeability ports 158 may permit gas to enter the distal tip 112 of the endoscope 100, for example, to sterilize one or more portions of the distal tip 112. In some embodiments, the gas permeability ports 158 may also include opaque reflective surfaces (e.g., opaque white surfaces), for example, to help maintain optimal light integration of the image sensor 156. In these, and other embodiments, a working channel may also be sterilized by this process.

The distal tip 112 includes an illumination channel 124 and a sensor channel 128. The illumination channel 124 includes the illumination source, such as an LED 152, the output of a fiber optic, or the like. The illumination channel 124 may provide a hollow tubing or other channeling mechanism that directs light emitted from the illumination source into the integrating sphere cap 120. In some embodiments, the illumination channel 124 may be manipulated by a physician or other user by using, for example, one or more screening elements disposed within the illumination channel 124 to block or impede light emitted from the illumination source directly reaching the sensor channel 128. The manipulation of the light source may enable the physician to alter the intensity of the illumination by the LED 152, such that varying amounts of light can be channeled into the integrating sphere cap 120 or into the operating theater.

The sensor channel 128 may direct the light exiting the integrating sphere cap 120 through the output port 148 onto an image sensor 156. While a single image sensor may be discussed herein, it is to be understood that additional or alternative image sensors may be used. Further, while the image sensor is depicted as disposed in the distal tip 112, the image sensor may be disposed in alternative locations of the endoscope 100 (e.g., within the endoscope body 104 or within the endoscope shaft 108). The image sensor 156, usually a CMOS or CCD sensor, includes a plurality of pixels 164, each containing a photodetector that converts detected light into an electric signal. The number and orientation of the pixels is not limited, and the plurality of pixels 164 may be disposed in, for example, and array. In some embodiments, the sensor channel 128 may be separated from the illumination channel 124, such that light emitted through the illumination channel 124 does not interfere with the measurements generated by the image sensor 156. Additionally, during a medical procedure, the image sensor 156 (or components of the endoscope 100 to which the image sensor 156 is connected) includes hardware and/or software for enabling collection of video or images of the medical procedure. In at least one exemplary embodiment, the image sensor 156 captures video and/or still images (or enables the capturing thereof) of an medical procedure being performed on a body of patient. As is known in the fields of endoscopy, arthroscopy, and the like, the image sensor 156 may be designed to enter a body and take real-time video of the procedure to assist the user (e.g., a physician) with performing the procedure and/or making diagnoses. In other embodiments, the image sensor 156 remains outside of the patient's body to capture images or video of an external medical procedure.

The integrating sphere cap 120 includes a light pipe 132, a reflective or mirrored surface 136, an input port 140, and an output port 148. The light pipe 132 may optionally receive light emitted from the illumination source (e.g., the LED 152), which may be distally placed in the elongated shaft 108. In some cases, the light may be channeled through the illumination channel 124. The integrating sphere cap 120 may be a substantially spherical (e.g., spherical with the exception of one or more additional curvatures, such as a curvature created by the mirrored surface 136) structure disposed on the end of the distal tip 112, such that the distal tip 112 is shielded from the outside environment, reducing the probability of contamination and maintaining the sterility of the distal tip until the cap is removed. While embodiments discussed herein are directed to receiving light from the illumination channel 124, alternative light sources may be used. For example, the light pipe 132 may channel light received from another illumination source external to the endoscope 100 (e.g., an LED, a laser, a flashlight, a lightbulb, etc.) that may be coupled to the light pipe 132 of the integrating sphere 120 or may be an appropriately positioned at a junction replacing the light pipe 132 and the mirrored surface 136 where an external illumination source may be connected, such as the distal interface of an illuminating optical fiber bundle. In such embodiments using an external light source, it is preferred that some physical barrier, such as a transparent window, be present at the junction, such that light may pass from the illumination source into the integrating sphere 120 but prevent any possible physical contamination to the distal tip 112 of the endoscope 100. In these implementations, the transparent window may be transparent in one direction, but reflective in the opposite direction, allowing light energy to pass into the integrated sphere, but not out of it. In more preferred embodiments, wherein the light pipe 132 is integrated into the integrating sphere cap 120, the light pipe 132 operates as a light guide that directs the light from the illumination channel 124 into the integrating sphere cap 120. The light pipe 132 may include one or more reflective coatings, mirrors, light fibers, plastic optical fibers, or combinations thereof, and the like to direct the light from the illumination channel 124 into an interior 134 of the integrating sphere cap 120, as illustrated with arrow 144. The light pipe 132 directs light from the illumination channel 124 onto the mirrored surface 136, which directs the light into the interior 134 of the integrating sphere cap 120. In some embodiments, the light pipe 132 may isolate the illumination channel 124 from the sensor channel 128, or from any other channel. For example, as illustrated in FIG. 1B, the light pipe 132 may be disposed in an upper portion of the integrating sphere cap 120 and include a barrier that separates the illumination channel 124 from the sensor channel 128, such that light emitted from the illumination channel 124 does not pass into and is not detected by sensors in the sensor channel 128, such as the image sensor 156. In other words, the light pipe 132 may separate (e.g., physically) light passing into the input port 140 of the integrating sphere cap 120 from light received from the output port 148 of the integrating sphere cap 120, which may beneficially enable improved readings or measurements of light passing through the output port 148 by ensuring directly emitted light is not included in the readings or measurements.

The interior 134 of the integrating sphere cap 120 may include one or more reflective surfaces and may additionally or alternatively include one or more reflective coatings that enable the light reflecting off the mirrored surface 136 to reflect within the integrating sphere cap 120, enabling the integrating sphere cap to operate as a customary integrating sphere, such as is known in the art, that is to provide uniform illumination to the image sensor 156. Additionally, an outside surface of the integrating sphere cap 120 may be opaque, or otherwise coated with a material that prevents light external to the integrating sphere cap 120 from passing into the integrating sphere cap 120. Alternatively or in addition, the integrating sphere cap 120 may be provided with a light-blocking cover, that is, a non-opaque integrating sphere cap 120 may be supplemented by a removable opaque covering, such as black plastic covering, which may be removed at an appropriate time during the calibration steps. As a result, the light propagating within the interior 134 of the integrating sphere cap 120 may be only the light emitted from the illumination source and passed into the integrating sphere cap 120 through the light pipe 132, and no light will be present or detectable to the image sensor while the integrating sphere cap is in place, except when the interior 134 is illuminated by the light source. As the light scatters within the integrating sphere cap 120, some light exits through the output port 148 and into the sensor channel 128. Upon entering the sensor channel 128, an imaging sensor 156 detects the light and generates a light reading or measurement. The image sensor 156 may use, for example, the one or more pixels 164 to capture light information and convert the light information into an electrical signal. The electrical signal may be passed to a processor, and may include information about the measured light, such as the intensity, frequency, Fixed Pattern Noise (FPN), combinations thereof, and the like. The FPN reading further includes a Dark Signal Non-Uniformity (DSNU) measurement, which represents the offset from the average of the noise across the pixels 164 in the image sensor 156 when the interior 134 of the integrating sphere is not illuminated, and a Photo Response Non-Uniformity (PRNU) measurement, which describes the gain between the optical power of each pixel and the output power of the electrical signal. One particular benefit of the integrating sphere cap is that its opaque outer surface prohibits light from entering the field of view of the image sensor 156, permitting a DSNU measurement, while the integrating sphere nature of the cap provides an ideal environment for a PRNU measurement, permitting, thereby, calibration of the endoscope's image sensor without exposing the distal tip region to the outside environment, thereby retaining a sterile environment within the distal tip region.

Figure 1C:
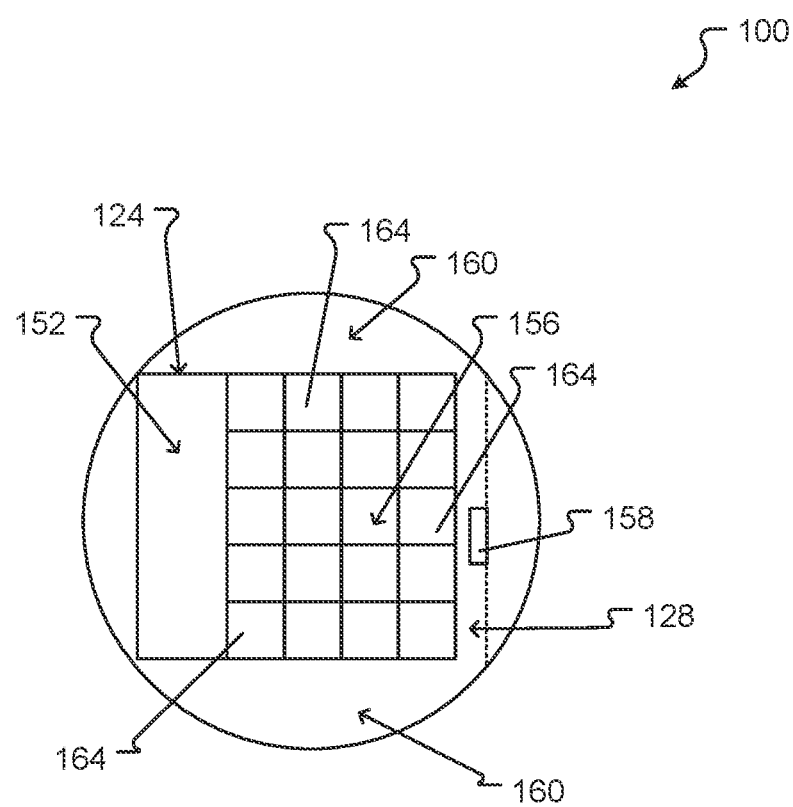
FIG. 1C illustrates a view of a distal tip of the endoscope according to at least one exemplary embodiment.

FIG. 1C illustrates a view of the distal tip 112 along the line A-A according to at least one exemplary embodiment. The view illustrates the LED 152 and the image sensor 156 disposed in the illumination channel 124 and the sensor channel 128, respectively. As previously discussed, the LED 152, or a plurality of LEDs, emits light that passes into the integrating sphere cap 120, while the image sensor 156 receives light exiting the integrating sphere cap 120 through the output port 148. The integrating sphere cap 120 and/or the distal tip 112 may include one or more keying surfaces 160 that facilitate the connection between the distal tip 112 and the integrating sphere cap 120. The keying surfaces 160 may include mechanical components (e.g., latches, keys, slots, gas permeability ports 158, etc.) that ensure a mating between the integrating sphere cap 120 and the distal tip 112 occur in a correct orientation. For example, the keying surfaces 160 on the distal tip 112 may include one or more female ports that permit corresponding male ports on the integrating sphere cap 120 to mechanically couple the integrating sphere cap 120 and the distal tip 112. In another example, the distal tip 112 may include one or more slots into which one or more lips on the integrating sphere cap 120 can enter to secure the integrating sphere cap 120 to the distal tip 112.

In some embodiments, the keying surfaces 160 may ensure that the integrating sphere cap 120 is and remains correctly attached and oriented to the distal tip 112, such as by preventing the output port 148 from aligning with the illumination channel 124. Stated differently, the keying surfaces 160 may ensure the illumination channel 124 is aligned with the light pipe 132 in the integrating sphere cap 120, so that light emitted through the illumination channel 124 enters the integrating sphere cap 120. In some embodiments, the keying surfaces 160 may contain an endoscopic working channel (not shown). In this case, the gas permeability ports 158 may be provided to ensure the working channel is properly sterilized during the sterilization of the endoscope 100 or for any other processing performed by, for example, a sterilization vendor. In some embodiments, the keying surfaces 160 may be aligned relative to the distal tip 112 and/or the integrating sphere cap 120 such that, when the integrating sphere cap 120 is connected to the distal tip 112, the integrating sphere cap 120 can be used to calibrate the endoscope 100. For example, the keying surfaces 160 may be positioned such that the illumination channel 124 and the sensor channel 128 are correctly aligned with the integrating sphere cap 120 to enable light passing through the illumination channel 124 to enter the integrating sphere cap 120 and exit through the sensor channel 128. It should also be noted that the connection between the distal tip 112 of the endoscope may be connected to the integrating sphere cap 120 in a semi-permanent or tamper evident way. That is, such that when the seal between the distal end of the endoscope and the integrating sphere cap 120 is broken, it will be evident to the user, and the cap cannot be replaced on the endoscope in such a way so as to disguise the prior disassembly. This objective of some embodiments may be achieved by any of the many means known in the art, such as by a foil covering, a breakable twist interface, and the like.

Figure 2:
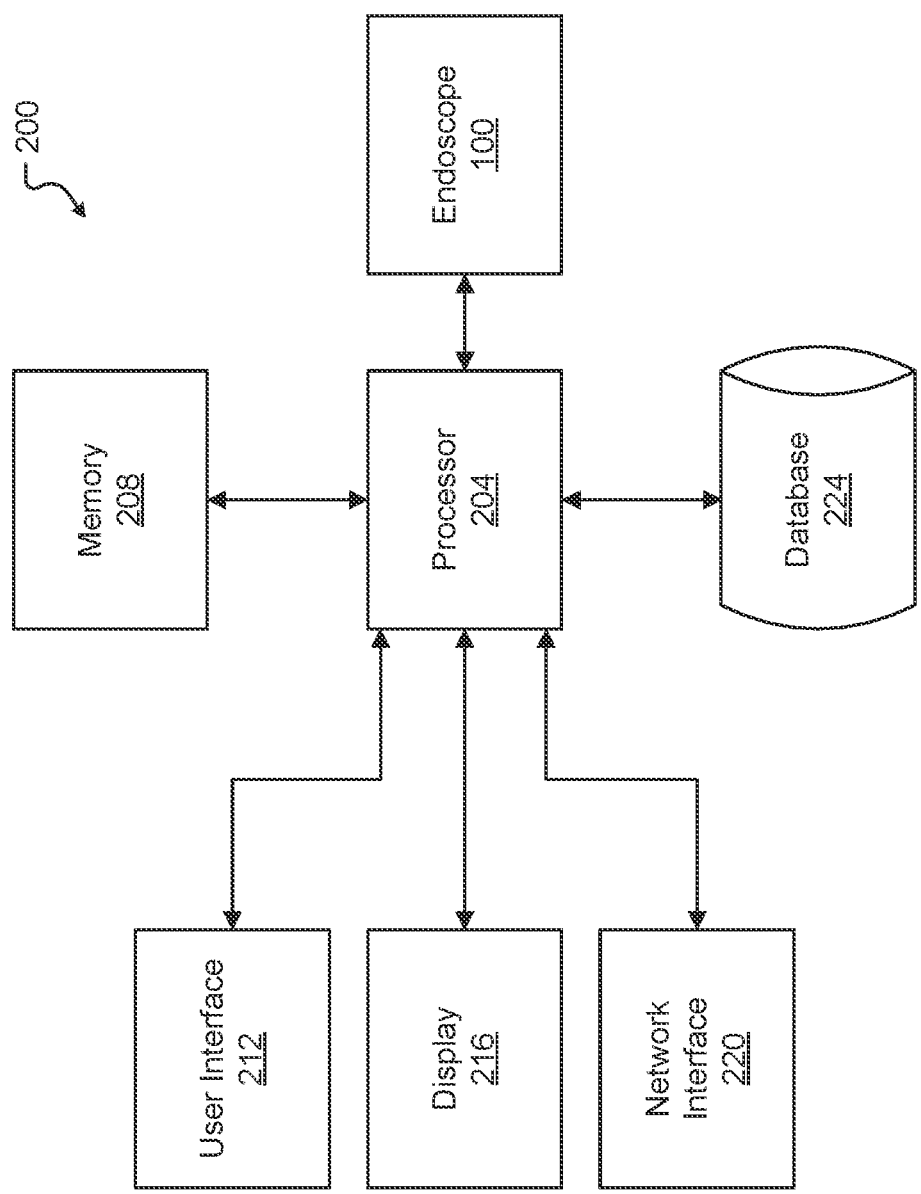
FIG. 2 illustrates a system according to at least one exemplary embodiment.

FIG. 2 illustrates a system 200 according to at least one exemplary embodiment. The system 200 includes the endoscope 100, a processor 204, a memory 208, a user interface 212, a display 216, a network interface 220, and a database 224. Notwithstanding the foregoing, the system 200 may include additional or alternative components, and may also omit one or more components shown. In some embodiments, the system 200 may correspond to the processing unit to which the endoscope 100 is connected.

The processor 204 may correspond to one or many computer processing devices. For instance, the processor 204 may be provided as a Field Programmable Gate Array (FPGA), an Application-Specific Integrated Circuit (ASIC), any other type of Integrated Circuit (IC) chip, a collection of IC chips, a microcontroller, a collection of microcontrollers, or the like. As a more specific example, the processor 204 may be provided as a microprocessor, Central Processing Unit (CPU), or plurality of microprocessors that are configured to execute the instructions sets stored in memory 208. The processor 204 enables various functions of the endoscope 100 and/or the system 200 upon executing the instructions stored in memory 208. The processor 204 may commonly be referred to as a Camera Control Unit (CCU).

The memory 208 may be or comprise a computer readable medium including instructions that are executable by the processor 204. The memory 208 may include any type of computer memory device and may be volatile or non-volatile in nature. In some embodiments, the memory 208 may include a plurality of different memory devices. Non-limiting examples of memory 208 include Random Access Memory (RAM), Read Only Memory (ROM), flash memory, Electronically-Erasable Programmable ROM (EE-PROM), Dynamic RAM (DRAM), etc. The memory 208 may include instructions that enable the processor 204 to control the various elements of the endoscope 100 and/or the system 200 and to store data, for example, into the database 224 and retrieve information from the database 224. The memory 208 may be local (e.g., integrated with) the processor 204 and/or separate from the processor 204.

The user interface 212 includes hardware and/or software that enables user input to the endoscope 100 and/or the system 200. The user interface 212 may include a keyboard, a mouse, a touch-sensitive pad, touch-sensitive buttons, mechanical buttons, switches, and/or other control elements for providing user input to the endoscope 100 and/or the system 200 to enable user control over certain functions of the endoscope 100 and/or the system 200 (e.g., operating lighting and/or imaging capabilities of the endoscope 100). The user interface may include buttons, switches, or other control means disposed on the endoscope 100 itself independent of or in addition to user interface controls not disposed on the endoscope. Simply as an illustrative example, the endoscope 100 may have input buttons and switches, and, additionally, a keyboard or mouse may be connected directly to the processor 204. Additionally, the display 216 may include touch screen capabilities, which are elements of the user interface 212. All of these together constitute the user interface 212.

The display 216 may be or comprise a liquid crystal display (LCD), a light emitting diode (LED) display, or the like. The display 216 may be a stand-alone display or a display integrated as part of another device, such as a smart phone, a laptop, a tablet, a headset or head-worn device, the CCU, and/or the like. In some embodiments, the display 216 may comprise a plurality of displays according to, for example, system design.

The database 224 includes the same or similar structure as the memory 208 described above. In at least one exemplary embodiment, the database 224 is included in a remote server and stores image data captured by the endoscope 100. The database and/or memory may also store calibration constants determined during the endoscope calibration process to be described below. It should be noted that the ability to store these calibration constants (e.g., on the processor 204, in the database 224, etc.) may obviate the need for the endoscope 100 to contain any memory and/or processing capabilities. This is particularly advantageous to SSU endoscopes and related systems, where waste (e.g., environmental impact) and cost can be reduced by omitting processing components from the SSU endoscope. Further, SSU endoscopes are often not designed to withstand an autoclave or other rigorous sterilization techniques. Accordingly, embodiments of the present disclosure beneficially provide a desirable solution for acquiring these calibration measurements without the risk of exposing the endoscope to contaminated (e.g., non-sterile) environments.

The network interface 220 may enable one or more components of the system 200 to communicate wired and/or wirelessly with one another or with the endoscope 100. These communication interfaces that permit the components of the system 200 to communicate using the network interface 220 include wired and/or wireless communication interfaces for exchanging data and control signals between one another. Examples of wired communication interfaces/connections include Ethernet connections, HDMI connections, connections that adhere to PCI/PCIe standards and SATA standards, and/or the like. Examples of wireless interfaces/connections include Wi-Fi connections, LTE connections, Bluetooth® connections, NFC connections, and/or the like.

Although FIG. 2 illustrates the various elements in the system 200 as being separate from one another, it should be appreciated that some or all of the elements may be integrated with each other if desired. For example, a single desktop or laptop computer may include the processor 204, the memory 208, the user interface 212, and the display 216. It should be further appreciated that each element in the system 200 includes one or more communication interfaces that enable communication with other elements in the system 200 over, for example, the network interface 220. Another example of a preferred embodiment of the system 200 includes an endoscope 100 with a built in user interface 212 connected to a CCU, the CCU comprising the memory 208, the processor 204, the network interface 220, and a user interface 212, and the CCU is also connected such that it can output image data to the display 216.

For illustrative purposes only, the following is an example of a method for calibrating an endoscopic system where the endoscope is a SSU endoscope. A SSU endoscope within a sterile package is received in a sterile operating room. A physician removes the endoscope from the packaging and connects the cable to a CCU. With the illumination source (in this example a distally placed LED) off, the CCU performs a DSNU measurement, determining the dark offset values of each of the pixels of the image sensor. These DSNU calibration constants are stored in the memory unit of the CCU. The CCU then turns on the light source, providing the integrating sphere cap with illumination, resulting in a uniform illumination being provided to the image sensor. The CCU then determines PRNU offset values of each of the pixels of the image sensor array. These PRNU calibration constants are stored in the memory unit of the CCU. The system indicates to the physician (e.g., on a display) that the calibration steps are now complete, at which time the physician may remove the integrating sphere cap from the endoscope, its distal tip remaining in a sterile environment until this time. The physician may now use the SSU endoscope to perform or assist in a medical procedure. Images captured by the image sensor are processed by the CCU using the DSNU and PRNU calibration constants in order to generate images of superior quality and/or clarity than would have been possible without the calibration steps. Of course, other FPN calibration steps may also be performed such as white balance, color correction, illumination optimization, etc. After the medical procedure is complete, the SSU endoscope may be disconnected from the CCU and discarded.

Figure 3:
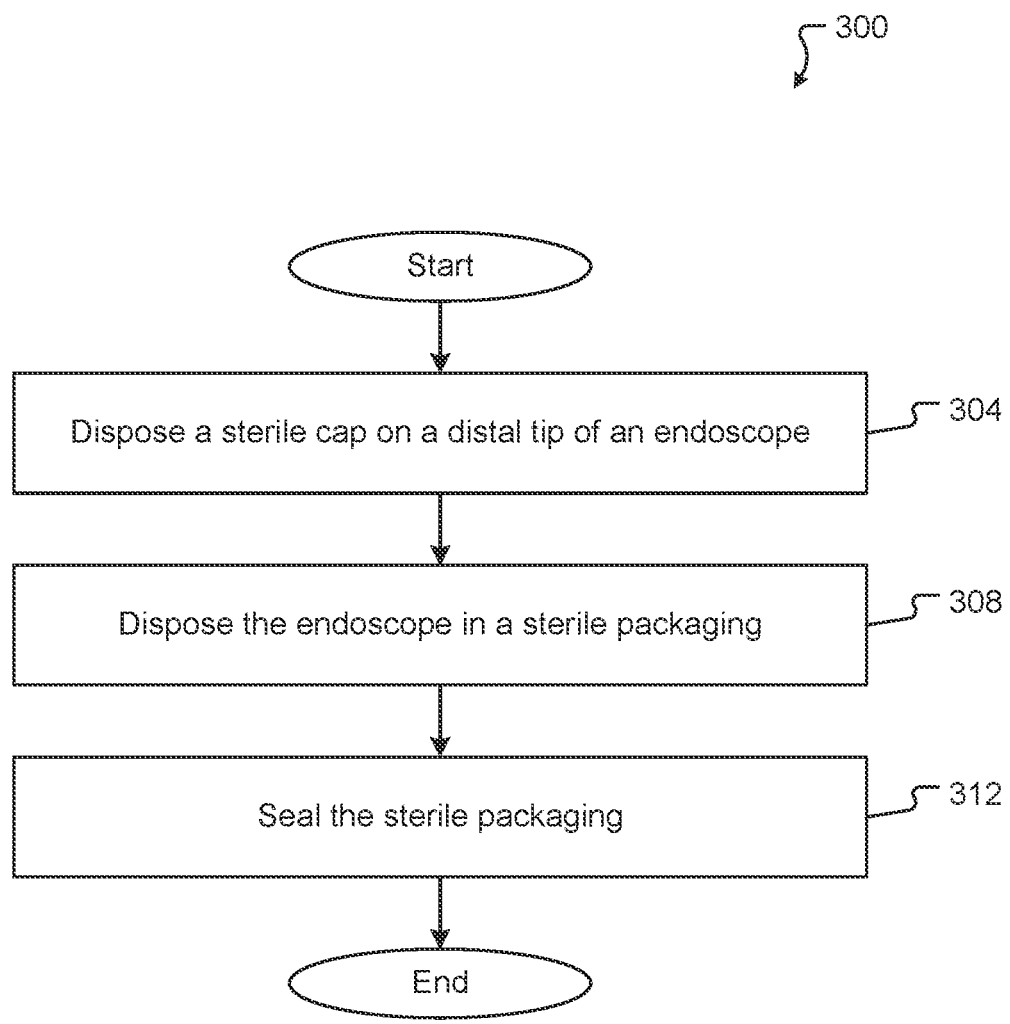
FIG. 3 illustrates a method for preparing an endoscope according to at least one exemplary embodiment.

FIG. 3 illustrates a method 300 according to at least one exemplary embodiment of the present disclosure. The method 300 may be used, for example, to dispose a sterile cap on an endoscope and package the endoscope for shipping.

The method 300 comprises disposing a sterile cap on a distal tip of an endoscope (step 304). The endoscope and the distal tip may be similar to or the same as the endoscope 100 and the distal tip 112, respectively. The sterile cap may be similar to or the same as the integrating sphere cap 120. In other embodiments, the sterile cap may include the integrating sphere cap 120 in addition to other components. In some embodiments, the sterile cap and the endoscope may be sterilized (e.g., immersed the components in heated water, autoclaved, soaked in a cleansing detergent, exposed to a sterilizing gas, etc.) and the sterile cap may be placed over the distal tip of the endoscope under sterile conditions, such that the sterile cap maintains the sterility of the distal tip of the endoscope even after the remainder of the endoscope is exposed to non-sterile environments. The connection between the sterile cap and the distal tip of the endoscope may indicated in a tamper evident manner, such as with a foil connector, a plastic bond that must be broken to remove the cap, or other means known in the art.

The method 300 also comprises disposing the endoscope in a sterile packaging (step 308). After the sterile cap has been disposed on the distal tip of the endoscope, the endoscope may be placed into a sterile packaging. In some embodiments, the sterile packaging may undergo similar or the same sterilization techniques as the endoscope.

The method 300 also comprises sealing the sterile packaging (step 312). The sealing may occur under sterile conditions, such that the endoscope remains sterile while in the sterile packaging, and is sterile when extracted from the sterile packaging, such as when the endoscope is used for a surgery, surgical procedure, or other medical procedure. In some embodiments, steps 304, 308 and 312 are all performed in a sterile environment, such that ideally the packaged endoscope remains in a fully sterile condition until it is opened in a prepared location, such as an operating room.

Figure 4:
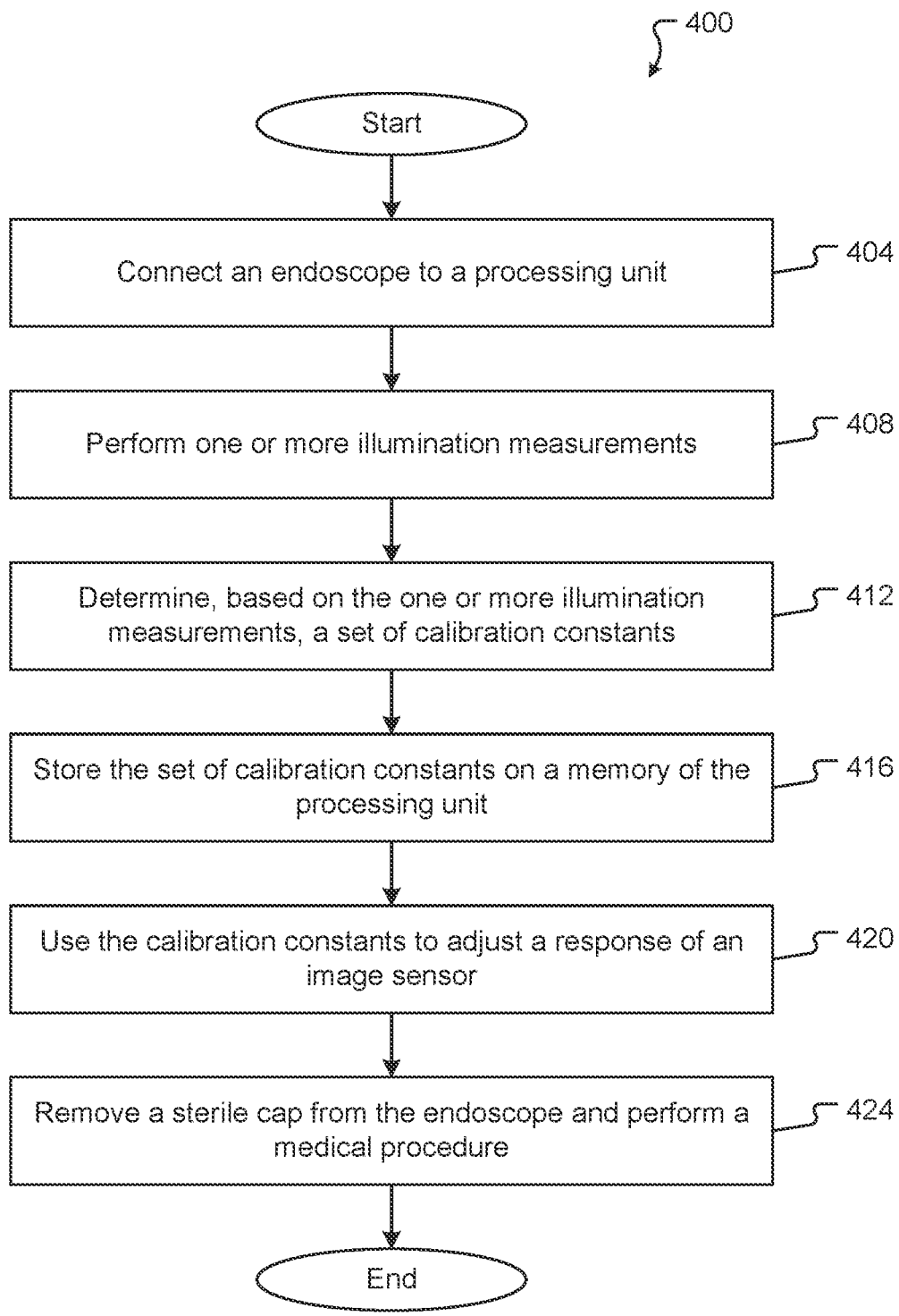
FIG. 4 illustrates a method for calibrating an endoscope according to at least one exemplary embodiment.

FIG. 4 illustrates a method 400 according to at least one exemplary embodiment of the present disclosure.

One or more steps of the method 400 may be carried out or otherwise performed, for example, by at least one processor. The at least one processor may be the same as or similar to the processor 204 of the system 200 as described above. A processor other than any processor described herein may also be used to execute one or more steps of the method 400. The at least one processor may perform one or more steps of the method 400 by executing elements stored in a memory such as the memory 208. The elements stored on the memory 208 (e.g., instructions and/or other data) and executed by the processor 204 may cause the processor 204 to execute one or more steps of the method 400.

The method 400 comprises connecting an endoscope to a processing unit (step 404). The endoscope may be similar to or the same as the endoscope 100, while the processing unit may include one or more components of the system 200 (e.g., the processor 204, the memory 208, the database 224, etc.). In some embodiments, the endoscope 100 may be connected to the processing unit through a wired connection (e.g., through the cable 116) and/or wirelessly, such as when the endoscope communicates with the processing unit through the network interface 220. In some embodiments, the step 404 may include connecting one or more other components to the endoscope 100, such as the display 216, an external illumination source (e.g., to emit light into the interior 134 of the integrating sphere cap 120), combinations thereof, and the like.

The method 400 also comprises performing one or more image sensor measurements (step 408). These measurements can be performed in accordance with an automated procedure controlled by the processor and/or manually at the request of a user. The processor 204 may cause an illumination source (e.g., the LED 152, an illumination source external to the endoscope 100, etc.) to emit light. The emitted light may pass through the illumination channel 124 and into the integrating sphere cap 120. The emitted light may be channeled into the interior 134 of the integrating sphere cap 120 through the light pipe 132. The channeled light may reflect off the mirrored surface 136 and into the interior 134 of the integrating sphere cap 120, where the light scatters off various interior surfaces of the integrating sphere cap 120. Eventually, the scattered light exits through the output port 148 and is passed into the sensor channel 128. Once in the sensor channel 128, the light is measured by the image sensor 156, which generates the one or more measurements, such as illumination measurements or image sensor readings. The illumination measurements or image sensor readings may be converted into electrical signals. The electrical signals may be passed to the processor 204 (e.g., wirelessly, through the cable 116, etc.), which may be programmed with instructions for decoding the electrical signals into one or more output parameters.

The method 400 also comprises determining, based on the one or more measurements, one or more sets of calibration constants (step 412). The one or more measurements are passed from the endoscope 100 to the processor 204, which determines a set of calibration constants. The calibration constants may be or comprise constants that can be used to adjust or otherwise calibrate the image sensor 156. For example, one calibration constant may be the magnitude of the electrical signal output by the image sensor 156 when receiving light exiting the integrating sphere cap 120. One of the objectives of such a calibration procedure is to calibrate the response of individual pixels 164 of the image sensor 156 under uniform illumination conditions, such as those provided in darkness (with no illumination) and those where an integrating sphere is illuminated, and this provides uniform illumination to each of the pixels 164 of the image sensor 156 array. Accordingly, one such calibration procedure may include a measurement of FPN, such as PRNU, by providing uniform illumination to each of the image sensor pixels, and deriving normalization constants for each pixel, resulting in the processor 204 being able to compensate for individual pixel variation under uniform illumination conditions. Likewise, another calibration procedure may include a measurement of DNSU by measuring the electrical response of each pixel under zero illumination conditions (such as those provided by the opaque integrating sphere cap when there is no illumination provided by the illumination source), resulting in the processor 204 determining dark offset values for each pixel, allowing, thereby, normalization constants to be determined for each pixel under zero illumination conditions. In some embodiments, these calibration constants can be used to calibrate the response of the image sensor 156 such that superior (that is, more true-to-life) images are able to be recorded and/or displayed, than would be possible with a non-calibrated system. It should be noted that the ability to store these calibration constants on the processor may obviate the need for memory and/or processing capabilities contained within the endoscope 100 itself. This is particularly advantageous to SSU systems, where a primary concern is to limit the necessary components of the disposable endoscope, thus reducing cost and decreasing the environmental impact. Further, it should be noted that SSU endoscopes are often not designed for the environment of an autoclave or other rigorous sterilization techniques, therefore a means by which these calibration measurements can be made without the risk of exposure to contaminants is greatly desirable.

The method 400 also comprises storing the set of calibration constants on a memory of the processing unit (step 416). The memory may correspond to the memory 208 of the system 200. In other words, the system 200 may correspond to the processing unit to which the endoscope 100 is connected, and the calibration constants may be stored on the memory 208. In some embodiments, the set of calibration constants may be stored on memory/database other than processing unit.

The method 400 also comprises using the calibration constants to adjust (automatically or manually) a response of an image sensor (step 420). The calibration constants may be or comprise information related to measured sensor readings of light exiting the integrating sphere cap 120 and measured by the image sensor 156. Such readings may contain information related to FPN, such as PRNU measurements. In order to compensate for the noise, the processing unit may adjust the image data received from the image sensor 156 such that image artifacts due to FPN is reduced. In some embodiments, the steps 408 through 420 may be repeated until the image sensor 156 has been calibrated (e.g., until the readings related to the FPN have been eliminated or reduced below a threshold required to operate the endoscope 100). Additionally or alternatively, the illumination source (e.g., the LED 152) may be adjusted. For example, the intensity of the LED 152 may be increased, reduced, or otherwise adjusted depending on the calibration constants. In some optional embodiments that can be used with any of the disclosed techniques or data, the adjustment may be or comprise applying one or more filters (e.g., low pass filters, bandpass filters, etc.) to the data received from the image sensor 156 to adjust the interpretation of the data. For example, a low pass filter may be applied to the data received from the image sensor 156 to help reduce the amount of noise in the data. The resulting data may be uploaded or displayed to a physician or other user on the user interface 212. The use of the filter may, for example, provide a clearer image of the light detected by the image sensor 156 and/or assist with image clarity and/or feature identification and/or visibility.

The method 400 also comprises removing a sterile cap from the endoscope and performing a medical procedure (step 424). The sterile cap (e.g., the integrating sphere cap 120) may be removed from the endoscope 100 in order to use the endoscope 100 in a surgery or other medical procedure. By removing the sterile cap just before the medical procedure, the distal tip 112 of the endoscope 100 remains sterile, beneficially enabling the endoscope 100 to be calibrated while avoiding exposing the endoscope 100 (and/or the distal tip 112 thereof) to possible contamination.

Although exemplary embodiments have been described with respect to medical procedures that occur internal to a patient, exemplary embodiments may also be applied to medical procedures that generally occur external to a patient.

In view of foregoing description, it should be appreciated that exemplary embodiments provide efficient methods for calibrating an endoscope without compromising the sterility of the endoscope. Methods and devices according to exemplary embodiments save time and cost and improve patient safety compared to related art.

At least one exemplary embodiment is directed to a device including an endoscope having a proximal end and a distal tip, the endoscope including an image sensor disposed at least partially in the distal tip; and a cap configured to be disposed on the distal tip of the endoscope, the cap including an integrating sphere.

Any of the features herein, wherein the integrating sphere includes a light pipe that receives light from a light source that is passed into an interior of the integrating sphere.

Any of the features herein, wherein the image sensor captures a first light reading, and wherein a processor determines, based on the first light reading, at least one of a Dark Signal Non-Uniformity (DSNU) measurement or a Photo Response Non-Uniformity (PRNU) measurement.

Any of the features herein, wherein the cap is aligned on the distal tip such that light propagating within the integrating sphere is captured by the image sensor.

Any of the features herein, wherein the light source is a light emitting diode (LED) in the distal tip of the endoscope.

Any of the features herein, wherein the light source is also a primary light source for the endoscope.

Any of the features herein, wherein a mirrored surface reflects the light passing through the light pipe into the interior of the integrating sphere.

Any of the features herein, wherein one or more keying surfaces are used to align the cap with the distal tip, aligning thereby the light source for the integrating sphere with the light pipe.

Any of the features herein, wherein an outside surface of the cap is opaque.

Any of the features herein, wherein the image sensor captures a first light reading, and wherein a processor determines, based on the first light reading, at least one of a Dark Signal Non-Uniformity (DSNU) measurement or a Photo Response Non-Uniformity (PRNU) measurement.

Any of the features herein, wherein the endoscope is a Sterile Single Use (SSU) endoscope.

Any of the features herein, wherein the cap is configured to maintain a sterile environment around the distal tip of the endoscope.

At least one exemplary embodiment is directed to a system including an endoscope having a proximal end and a distal tip; an image sensor disposed in the distal tip; an integrating sphere cap configured to be disposed on the distal tip and further configured to be removed from the distal tip; a processor; and a memory storing data thereon that, when processed by the processor, cause the processor to: produce light from an illumination source disposed within the endoscope; and receive a first light reading from the image sensor.

Any of the features herein, wherein the illumination source includes a light emitting diode (LED), and wherein the integrating sphere cap includes a light pipe that channels the light produced by the LED into an interior of the integrating sphere cap.

Any of the features herein, wherein a mirrored surface reflects the light passing through the light pipe into the interior of the integrating sphere cap.

Any of the features herein, wherein the integrating sphere cap is aligned with the distal tip with at least one keying surface such that the light emitted by the LED is directed to the light pipe, and wherein light propagating within the integrating sphere cap is measured by the imaging sensor.

Any of the features herein, wherein the integrating sphere cap is substantially spherical, and wherein the light pipe isolates the LED from the image sensor.

Any of the features herein, wherein the data further cause the processor to calibrate the image sensor, and wherein the calibrating of the image sensor further comprises: determining, based on the first light reading, data related to a Fixed Noise Pattern (FNP); and determining, based on the data, a first adjustment to an interpretation of image data received from the image sensor to compensate for the FNP.

Any of the features herein, wherein the FNP includes at least one of a Dark Signal Non-Uniformity (DSNU) measurement or a Photo Response Non-Uniformity (PRNU) measurement.

At least one exemplary embodiment is directed to a method including emitting light from an illumination source disposed in an endoscope; receiving a first reading from an image sensor disposed in the endoscope, the first reading based on the light emitted from the illumination source and passed through an integrating sphere cap fixedly connected to the endoscope; and calibrating, based on the first reading, a response of the image sensor.

Any of the features herein, wherein the integrating sphere cap includes a light pipe configured to channel the light emitted from the illumination source onto a mirrored surface that reflects the light into an interior of the integrating sphere cap.

Any of the features herein, wherein the first reading includes information about at least one of a Dark Signal Non-Uniformity (DSNU) measurement or a Photo Response Non-Uniformity (PRNU) measurement.

Any of the features herein, further comprising: determining, based on the first reading, a first adjustment to an interpretation of image data received from the image sensor to compensate for the DSNU measurement or for the PRNU measurement.

At least one exemplary embodiment is directed to a method for calibrating and preparing to operate a sterile single use (SSU) endoscope, the method including disposing the endoscope in a sterile packaging, the endoscope comprising a removable cap covering a distal tip of the endoscope and the removable cap including an integrating sphere; and sealing the sterile packaging, wherein the endoscope is configured to: connect to a processing unit, and perform a Dark Signal Non-Uniformity (DSNU) measurement.

Any of the features herein, wherein the endoscope is further configured to: illuminate, with a light emitting diode (LED) disposed within the distal tip, the integrating sphere; perform a Photo Response Non-Uniformity (PRNU) measurement; and store a set of calibration constants on a memory of the processing unit.

Any of the features herein, wherein the removable cap is configured to be removable from the distal tip of the endoscope to expose the distal tip.

Any of the features herein, wherein the integrating sphere includes a light pipe that cannels the light produced by the LED into an interior of the integrating sphere.

Any of the features herein, wherein the LED is also a primary light source for the endoscope.

Any of the features herein, wherein the integrating sphere includes a mirrored surface that reflects the light passing through the light pipe into the interior of the integrating sphere.

Any of the features herein, wherein an outside surface of the removable cap is opaque.

At least one exemplary embodiment is directed to a device including an endoscope having a proximal end and a distal tip, the endoscope including an image sensor disposed at least partially in the distal tip; and a sterile spherical cap configured to be disposed on the distal tip of the endoscope and further configured to facilitate calibration of the image sensor.

At least one exemplary embodiment is directed to a sterile spherical cap configured to be disposed on a distal tip of an endoscope and further configured to facilitate calibration of an image sensor, the sterile spherical cap including: an integrating sphere; and an attachment mechanism configured to attach the sterile spherical cap to the distal tip of the endoscope.

Any feature in combination with any one or more other features.

Any one or more of the features disclosed herein

Any one or more of the features as substantially disclosed herein.

Any one or more of the features as substantially disclosed herein optionally in combination with any one or more other features as substantially disclosed herein.

One or more means adapted to perform any one or more of the above features as substantially disclosed herein.

It is to be appreciated that any feature described herein can be claimed in combination with any other feature(s) as described herein, regardless of whether the features come from the same described embodiment.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

Aspects of the present disclosure may take the form of an embodiment that is entirely hardware, an embodiment that is entirely software (including firmware, resident software, micro-code, etc.) or an embodiment combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

The terms "determine," "calculate," "compute," and variations thereof, as used herein, are used interchangeably and include any type of methodology, process, mathematical operation or technique.

Exemplary embodiments may be configured according to the following:

(1) A device, comprising:
   an endoscope having a proximal end and a distal tip, the endoscope including an image sensor disposed at least partially in the distal tip; and
   a cap configured to be disposed on the distal tip of the endoscope, the cap including an integrating sphere.

(2) The device of (1), wherein the integrating sphere includes a light pipe that receives light from a light source that is passed into an interior of the integrating sphere.

(3) The device of one or more of (1) or (2), wherein the image sensor captures a first light reading, and wherein a processor determines, based on the first light reading, at least one of a Dark Signal Non-Uniformity (DSNU) measurement or a Photo Response Non-Uniformity (PRNU) measurement.

(4) The device of any one or more of (1) to (3), wherein the cap is aligned on the distal tip such that light propagating within the integrating sphere is captured by the image sensor.

(5) The device of any one or more of (1) to (4), wherein the light source is a light emitting diode (LED) in the distal tip of the endoscope.

(6) The device of any one or more of (1) to (5), wherein the light source is also a primary light source for the endoscope.

(7) The device of any one or more of (1) to (6), wherein a mirrored surface reflects the light passing through the light pipe into the interior of the integrating sphere.

(8) The device of any one or more of (1) to (7), wherein one or more keying surfaces are used to align the cap with the distal tip, aligning thereby the light source for the integrating sphere with the light pipe.

(9) The device of any one or more of (1) to (8), wherein an outside surface of the cap is opaque

(10) The device of any one or more of (1) to (9), wherein the image sensor captures a first light reading, and wherein a processor determines, based on the first light reading, at least one of a Dark Signal Non-Uniformity (DSNU) measurement or a Photo Response Non-Uniformity (PRNU) measurement.
(11) The device of any one or more of (1) to (10), wherein the endoscope is a Sterile Single Use (SSU) endoscope.
(12) The device of any one or more of (1) to (11), wherein the cap is configured to maintain a sterile environment around the distal tip of the endoscope.
(13) A system, comprising:
an endoscope having a proximal end and a distal tip;
an image sensor disposed in the distal tip;
an integrating sphere cap configured to be disposed on the distal tip and further configured to be removed from the distal tip;
a processor; and
a memory storing data thereon that, when processed by the processor, cause the processor to:
produce light from an illumination source disposed within the endoscope; and
receive a first light reading from the image sensor.
(14) The system of (13), wherein the illumination source includes a light emitting diode (LED), and wherein the integrating sphere cap includes a light pipe that channels the light produced by the LED into an interior of the integrating sphere cap.
(15) The system of any one or more of (13) to (14), wherein a mirrored surface reflects the light passing through the light pipe into the interior of the integrating sphere cap.
(16) The system of any one or more of (13) to (15), wherein the integrating sphere cap is aligned with the distal tip with at least one keying surface such that the light emitted by the LED is directed to the light pipe, and wherein light propagating within the integrating sphere cap is measured by the imaging sensor.
(17) The system of any one or more of (13) to (16), wherein the integrating sphere cap is substantially spherical, and wherein the light pipe isolates the LED from the image sensor.
(18) The system of any one or more of (13) to (17), wherein the data further cause the processor to calibrate the image sensor, and wherein the calibrating of the image sensor further comprises:
determining, based on the first light reading, data related to a Fixed Noise Pattern (FNP); and
determining, based on the data, a first adjustment to an interpretation of image data received from the image sensor to compensate for the FNP.
(19) The system of any one or more of (13) to (18), wherein the FNP includes at least one of a Dark Signal Non-Uniformity (DSNU) measurement or a Photo Response Non-Uniformity (PRNU) measurement.
(20) A method, comprising:
emitting light from an illumination source disposed in an endoscope;
receiving a first reading from an image sensor disposed in the endoscope, the first reading based on the light emitted from the illumination source and passed through an integrating sphere cap fixedly connected to the endoscope; and
calibrating, based on the first reading, a response of the image sensor.
(21) The method of (20), wherein the integrating sphere cap includes a light pipe configured to channel the light emitted from the illumination source onto a mirrored surface that reflects the light into an interior of the integrating sphere cap.
(22) The method of any one or more of (20) to (21), wherein the first reading includes information about at least one of a Dark Signal Non-Uniformity (DSNU) measurement or a Photo Response Non-Uniformity (PRNU) measurement.
(23) The method of any one or more of (20) to (22), further comprising:
determining, based on the first reading, a first adjustment to an interpretation of image data received from the image sensor to compensate for the DSNU measurement or for the PRNU measurement.
(24) A method for calibrating and preparing to operate a sterile single use (SSU) endoscope, the method comprising:
disposing the endoscope in a sterile packaging, the endoscope comprising a removable cap covering a distal tip of the endoscope and the removable cap including an integrating sphere; and
sealing the sterile packaging, wherein the endoscope is configured to:
connect to a processing unit, and
perform a Dark Signal Non-Uniformity (DSNU) measurement.
(25) The method of (24), wherein the endoscope is further configured to:
illuminate, with a light emitting diode (LED) disposed within the distal tip, the integrating sphere;
perform a Photo Response Non-Uniformity (PRNU) measurement; and
store a set of calibration constants on a memory of the processing unit.
(26) The method of any one or more of (24) to (25), wherein the removable cap is configured to be removable from the distal tip of the endoscope to expose the distal tip.
(27) The method of any one or more of (24) to (26), wherein the integrating sphere includes a light pipe that cannels the light produced by the LED into an interior of the integrating sphere.
(28) The method of any one or more of (24) to (27), wherein the LED is also a primary light source for the endoscope.
(29) The method of any one or more of (24) to (28), wherein the integrating sphere includes a mirrored surface that reflects the light passing through the light pipe into the interior of the integrating sphere.
(30) The method of any one or more of (24) to (29), wherein an outside surface of the removable cap is opaque.
(31) A device, comprising:
an endoscope having a proximal end and a distal tip, the endoscope including an image sensor disposed at least partially in the distal tip; and
a sterile spherical cap configured to be disposed on the distal tip of the endoscope and further configured to facilitate calibration of the image sensor.
(32) A sterile spherical cap configured to be disposed on a distal tip of an endoscope and further configured to facilitate calibration of an image sensor, the sterile spherical cap comprising:
an integrating sphere; and
an attachment mechanism configured to attach the sterile spherical cap to the distal tip of the endoscope.

What is claimed is:

1. A device, comprising:
   an endoscope having a proximal end and a distal tip, the endoscope including an image sensor disposed at least partially in the distal tip; and
   a cap configured to be disposed on the distal tip of the endoscope, the cap including an integrating sphere, the integrating sphere including a light pipe configured to receive light from a light source that is passed into an interior of the integrating sphere, the cap sealed to the distal tip and configured to maintain a sterile state of the distal tip of the endoscope until after the integrating sphere is used to calibrate the endoscope.

2. The device of claim 1, wherein the image sensor captures a first light reading, and wherein a processor determines, based on the first light reading, at least one of a Dark Signal Non-Uniformity (DSNU) measurement or a Photo Response Non-Uniformity (PRNU) measurement.

3. The device of claim 1, wherein the cap is aligned on the distal tip such that light propagating within the integrating sphere is captured by the image sensor.

4. The device of claim 1, wherein the light source is a light emitting diode (LED) in the distal tip of the endoscope.

5. The device of claim 4, wherein the light source is also a primary light source for the endoscope.

6. The device of claim 4, wherein one or more keying surfaces are used to align the cap with the distal tip, aligning thereby the light source for the integrating sphere with the light pipe.

7. The device of claim 1, wherein an outside surface of the cap is opaque.

8. The device of claim 7, wherein the image sensor captures a first light reading, and wherein a processor determines, based on the first light reading, at least one of a Dark Signal Non-Uniformity (DSNU) measurement or a Photo Response Non-Uniformity (PRNU) measurement.

9. The device of claim 1, wherein the cap is configured to maintain a sterile environment around the distal tip of the endoscope until a seal is broken.

10. A system, comprising:
    an endoscope having a proximal end and a distal tip;
    an image sensor disposed in the distal tip;
    an integrating sphere cap, that includes a light pipe configured to receive light from an illumination source that is passed into an interior of the integrating sphere cap, configured to be disposed on the distal tip and further configured to be removed from the distal tip, the cap sealed to the distal tip and configured to maintain a sterile state of the distal tip of the endoscope until after the integrating sphere cap is used to calibrate the endoscope;
    a processor; and
    a memory storing data thereon that, when processed by the processor, cause the processor to:
       produce light from the illumination source disposed within the endoscope; and
       receive a first light reading from the image sensor to calibrate the endoscope.

11. The system of claim 10, wherein the illumination source includes a light emitting diode (LED), and wherein the integrating sphere cap includes a light pipe that channels the light produced by the LED into an interior of the integrating sphere cap.

12. The system of claim 11, wherein a mirrored surface reflects the light passing through the light pipe into the interior of the integrating sphere cap.

13. The system of claim 12, wherein the integrating sphere cap is aligned with the distal tip with at least one keying surface such that the light emitted by the LED is directed to the light pipe, and wherein light propagating within the integrating sphere cap is measured by the imaging sensor.

14. The system of claim 13, wherein the integrating sphere cap is substantially spherical, and wherein the light pipe isolates the LED from the image sensor.

15. The system of claim 12, wherein the data further cause the processor to calibrate the image sensor, and wherein the calibrating of the image sensor further comprises:
    determining, based on the first light reading, data related to a Fixed Noise Pattern (FNP); and
    determining, based on the data, a first adjustment to an interpretation of image data received from the image sensor to compensate for the FNP.

16. The system of claim 15, wherein the FNP includes at least one of a Dark Signal Non-Uniformity (DSNU) measurement or a Photo Response Non-Uniformity (PRNU) measurement.

17. A method for calibrating and preparing to operate a sterile single use (SSU) endoscope, the method comprising:
    disposing the endoscope in a sterile packaging, the endoscope comprising a removable cap covering a distal tip of the endoscope and the removable cap including an integrating sphere,
    sealing the removable cap to the distal tip to maintain a sterile state of the distal tip of the endoscope until after the integrating sphere is used to calibrate the endoscope; and
    sealing the sterile packaging, wherein the endoscope is configured to:
       connect to a processing unit, and
       perform a Dark Signal Non-Uniformity (DSNU) measurement.

18. The method of claim 17, wherein the endoscope is further configured to:
    illuminate, with a light emitting diode (LED) disposed within the distal tip, the integrating sphere;
    perform a Photo Response Non-Uniformity (PRNU) measurement; and
    store a set of calibration constants on a memory of the processing unit.

19. The method of claim 18, wherein the removable cap is configured to be removable from the distal tip of the endoscope to expose the distal tip.

* * * * *